(12) United States Patent
Lönne

(10) Patent No.: US 6,712,839 B1
(45) Date of Patent: Mar. 30, 2004

(54) FRAME AND METHOD FOR SUTURING OF A WOUND

(76) Inventor: Greger Lönne, Rindabuvn. 18, N-2322 Rindabu (NO)

( * ) Notice: Subject to any disclaimer, the term of this patent is extended or adjusted under 35 U.S.C. 154(b) by 73 days.

(21) Appl. No.: 09/959,611
(22) PCT Filed: Nov. 23, 2000
(86) PCT No.: PCT/NO00/00396
§ 371 (c)(1), (2), (4) Date: Nov. 1, 2001
(87) PCT Pub. No.: WO01/37740
PCT Pub. Date: May 31, 2001

(30) Foreign Application Priority Data

Nov. 24, 1999 (NO) .......................................... 1999-5755

(51) Int. Cl.[7] ................................................ A61B 17/04
(52) U.S. Cl. ........................ 606/233; 606/215; 606/216
(58) Field of Search ............................... 606/215, 216, 606/233

(56) References Cited

U.S. PATENT DOCUMENTS

| | | | | |
|---|---|---|---|---|
| 363,538 A | * | 5/1887 | Penny | 606/215 |
| 1,428,495 A | | 9/1922 | Radcliffe | |
| 1,774,489 A | | 8/1930 | Sarason | |
| 2,371,978 A | * | 3/1945 | Perham | 606/216 |
| 3,014,483 A | * | 12/1961 | McCarthy | 606/233 |
| 3,648,705 A | * | 3/1972 | Lary | 606/233 |
| 3,695,271 A | * | 10/1972 | Chodorow | 606/233 |
| 3,831,608 A | * | 8/1974 | Kletschka et al. | 606/233 |
| 3,926,193 A | | 12/1975 | Hansson | |
| 3,934,592 A | * | 1/1976 | Wolvek et al. | 606/233 |
| 4,539,990 A | | 9/1985 | Stivala | |
| 5,176,703 A | | 1/1993 | Peterson | |
| 5,843,123 A | | 12/1998 | Brazeau | |

FOREIGN PATENT DOCUMENTS

| | | |
|---|---|---|
| EP | 0396274 | 11/1990 |
| JP | 6-247847 | 9/1994 |
| WO | 9012912 | 11/1990 |

* cited by examiner

*Primary Examiner*—Gary Jackson
(74) *Attorney, Agent, or Firm*—Wenderoth, Lind & Ponack, L.L.P.

(57) ABSTRACT

A frame (1) and a method for suturing a wound (22). The frame (1) is placed on each side of the wound (22) and reaches across it. The frame (1) has a first and second foundation part (2, 3) for placing on the skin (20) on each side and along the wound/wound edges respectively. A joining device extends (10) between the first and second foundation parts (2, 3). The first and second foundation parts (2, 3) are arranged with an adhesive (4, 5) for securing to the skin (20), and the joining device (10) is a flexible, jointed device of mainly constant length.

14 Claims, 3 Drawing Sheets

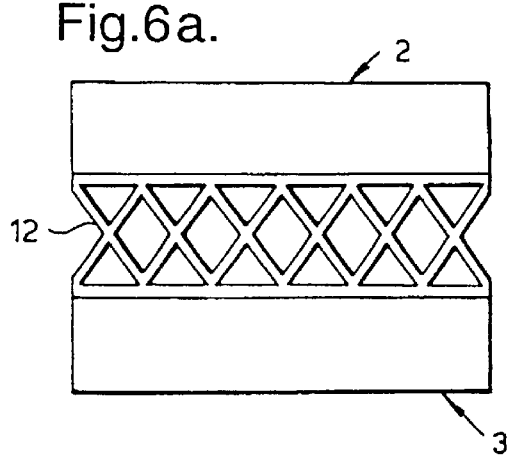
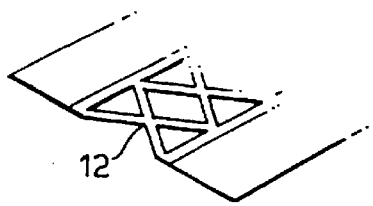
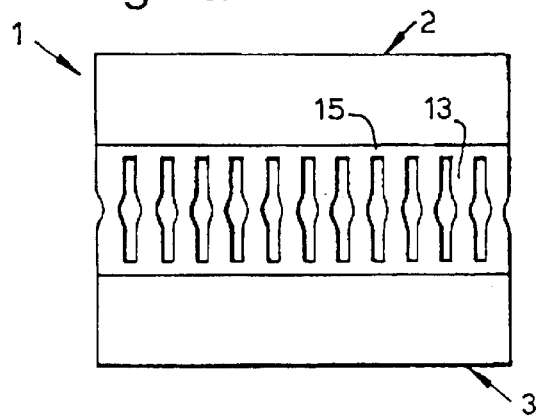
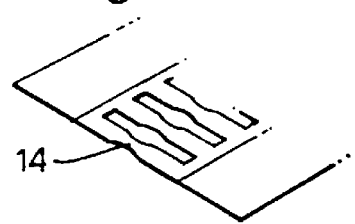
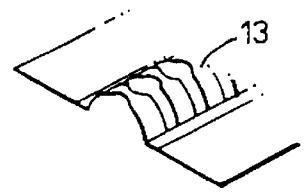
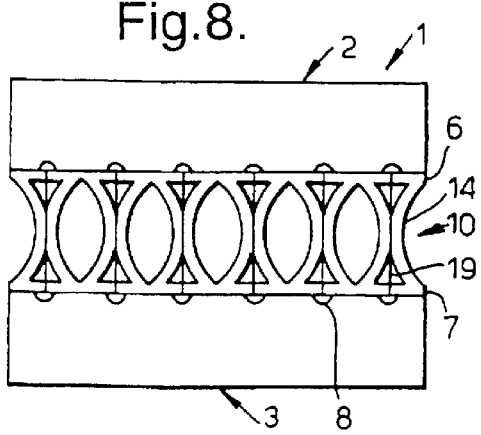
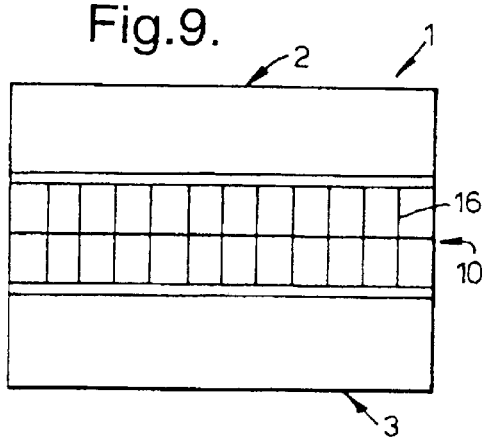

FRAME AND METHOD FOR SUTURING OF A WOUND

This application is a national stage entry of PCT/NO00/00396, filed Nov. 23, 2000.

BACKGROUND OF THE INVENTION

This invention concerns a frame for use in suturing a wound where the frame is placed on each side of the wound and reaches over it. The frame includes a first and second foundation part for placing on the skin on each side of an along the wound, wound edges respectively, and a joining device between the first and second foundation parts.

Further, the invention concerns a method for suturing a wound by help of the above-mentioned frame.

Removal of moles/birthmarks and other minor operations performed on the upper body, upper arms and thighs can result in wide and ugly scars. The reasons for this are several, but the scars seem to be affected by the tension across the wound during the healing phase, the tightening and placing of the stitches, as well as the length of time the stitches remain in the skin. In addition, any infection in the wound will cause an uglier scar.

When a wound grows, it is important that the skin at the wound edges is sufficiently suited to each other (lying edge to edge) for optimal healing and minimal risk of infection. This is traditionally performed by different suture techniques. Stitches are necessary for adaption during the first part of the healing of the wound, but the stitches also leave marks and play a role in the final appearance of the scar. Sutures that are not too tight and not left in the wound too long, but lengthy, good and stable adaption of the skin edge, are therefore contradictory elements for optimal healing of a wound. Due to the elasticity and therefore the tension in the skin in some areas of the body, it is difficult to meet both criteria. Healing will either result in emphasized suture marks due to lengthy suture time, or the wound splits opens due to the sutures being removed too soon, and a stretch forces the wound edges apart. Stitches in the skin are also an entrance for bacteria, which can cause infections.

Varying techniques are used today to reduce the marks left by sutures.

Intradermal suture, suture tape and tissue adhesive are examples of these. On parts of the body with low tension in the skin, these arrangements are sufficient to hold the wound edges together until they have healed (stomach, face). On the upper body and the limbs, however, the tension is so great that it is difficult to keep the wound edges together with these arrangements. It is extra difficult for young doctors lacking experience and competence in suturing techniques. Subsequently, the wound often splits open. If one closes a wound by sewing in the traditional manner, with single stitches across the wound, the stitches often have to remain in place for 12–14 days before they can be removed. This often results in disfiguring suture marks. If the stitches are removed earlier, to avoid suture marks, the scar splits open and becomes wide and disfiguring.

One supplier of suture equipment within the area of the present invention is Johnson & Johnson, and in their "Wound Closure Manual" there is a description of sutures and equipment used to reduce the tension across the scar during suturing. A short resume of this suturing equipment will now be given.

"Retention Suture Bridge" described in U.S. Pat. No. 4,275,736 is a wide hollow plastic rib which is placed across the wound and which, with the help of a large needle, is fastened with sutures through the wound. This is to avoid necrosis in the skin around the stitch placed in the area with extreme tension, or to avoid them cutting through the skin. One disadvantage with this "suture bridge" is that it requires extra stitches, which in turn cause scars. It lies directly against the wound and must be removed when the wound is cleaned, and it needs the suture to keep it in place. Further, the suture bridge does not distribute the tension evenly over the whole scar, but rather distributes most of the tension in the middle and decreasingly outwards towards the ends. The equipment is designed to prevent tissue necrosis/dead tissue or the skin sutures cutting through the wound edges.

"Retention Suture Bolsters" are latex tubes which are placed across the wound and which the stitches are sewn round. This prevents the sutures lying directly on the skin and thus prevents suture marks. The problem is that the sutures have to remain there for 14 days and thus cause irritation around the scar. The method is little used, since it tends to cause infection around the wound and to cause necrosis if tightened too much. Furthermore, it causes poor airing and moisture removal.

"Skin Closure Tape" is a reinforced plaster, which is glued across the wound and which either alone, or with sutures, is intended to keep the wound edges together. The plaster is not strong enough alone to hold the wound edges together in areas with high tension in the skin, but when used together with sutures, it can help relieve the tension somewhat. When the stitches are removed, the plaster has to be removed, and it is often soaked with blood and has to be changed. One can always remove the stitches early and alternatively set new tape on, but one runs the risk of the scar reopening before the new tape is in place. The area will additionally be exposed to tension along the scar because the tape only stabilizes across the scar.

Another type of suture equipment on the market is the so-called "zip" (Medizip). This is placed on each side of the wound with tape and the zip is then closed. The tension across the wound will be reduced, but does not allow for checking the wound, as the wound cannot be seen without opening the zip. Neither can it be combined with the suture material, with the result that this equipment is difficult to use on skin where the tension is great, where skin has been removed, for example, in connection with the removal of moles.

U.S. Pat. No. 3,934,592 ("Suture Bridge") is designed to prevent the sutures digging themselves down and causing necrosis in the skin during the closing of larger incisions, in particular after surgery on the abdomen/stomach. It lifts the sutures off the skin and distributes tension across the ribs, which lie along the scar. The aim here, as with the "Retention Suture Bridge" is to reduce the pull across the crossing stitches. This is to prevent necrosis in the skin around stitches set in areas of great tension, or to prevent them cutting into the skin. One drawback with this method is that it requires sutures to be kept in place. Further, it is not intended to be used with the intradermal method. The sutures have to be placed across the wound, which means there are many prick-like scars. The equipment is intended to prevent tissue necrosis or the skin sutures cutting into the edge of the wound in a larger scar with extreme tension.

SUMMARY OF THE INVENTION

One object of the present invention is to provide a suture frame which can stay in place by itself and create an area with low tension around the closed wound. This allows one to keep the wound edges together when using the intradermal technique. Further, it should be possible to check the pull in the thread easily, which can be difficult when one attaches the thread directly to the skin. Without the frame, strong pull will result in a puckering effect across the wound, because thread is attached to the skin on each side, and too loose tension will result in the wound splitting.

Another object of the invention is that the suture equipment is kept away from the wound itself, to avoid it growing into the wound.

Another object of the invention of the invention is that the suture equipment allows one to inspect the wound and remove the stitches without removing the suture frame itself, after a relatively short period of time (5–7 days).

Another object of the invention of the invention is that the frame in addition to the intradermal suture can also be used on normal, single sutures.

A further object of the invention is that the suture equipment is designed to allow airing of, and moisture removal from the wound. The wound should be easily accessible but at the same time be protected from pulling in all directions.

The above-mentioned objects are met according to the invention by a frame for use during suturing of a wound, where the frame is placed on each side of the wound and reaches across it, in that the frame comprises:

a first and second foundation part for placing on the skin on each side of and along the wound/wound edges respectively, and a joining device between the first and second foundation part, characterised in that the first and second foundation part is arranged with an adhesive for fastening to the skin, and the joining device consists of a flexible, jointed device with mainly constant length.

The objects of the invention are achieved by a method for suturing of a wound with help of a frame, where the frame is placed on each side of the wound and reaches across this and where the frame comprises;

a first and second foundation part for placing and attaching to the skin on each side and along the wound/wound edges respectively, and a joining device between the first and second foundation parts, wherein the wound is closed by intracutan suture technique, in that the threads are not attached to the skin and remain loose, the wound is pulled together, the frame is placed on each side of the wound and is attached by means of an adhesive on the first and second foundation parts respectively, whereby low tension around the closed wound is achieved, and the threads are pulled up and tied across the joining device which consists of a joined construction with mainly constant length, whereby the pull in the threads is controlled.

BRIEF DESCRIPTION OF THE DRAWINGS

The invention will now be explained with reference to the enclosed figures, where:

FIGS. 6a and 6b show another embodiment of the frame seen respectively from above and from a short end thereof;

FIGS. 7a, 7b and 7c show a third embodiment of the frame seen from above and from a short end thereof;

FIG. 8 shows a fourth embodiment of the frame; and

FIG. 9 shows a fifth embodiment of the frame.

DETAILED DESCRIPTION OF THE INVENTION

A method for suturing of a wound 22 by means of a frame 1 according to the present invention will now be explained with reference first to FIGS. 1a to 1e.

Figure 1A:
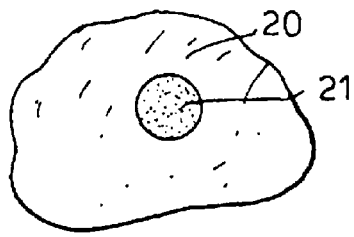
FIGS. 1a, 1b, 1c, 1d and 1e show a method for suturing a wound by means of a first embodiment of a frame constructed in accordance with the invention.
Figure 1B:
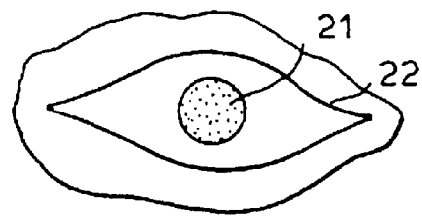
Figure 1C:
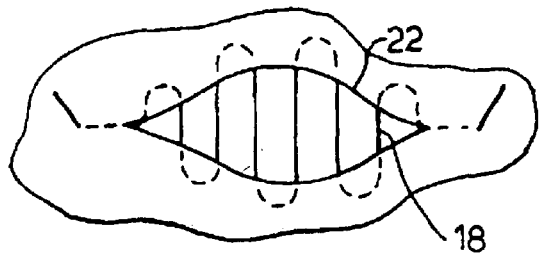
Figure 1D:
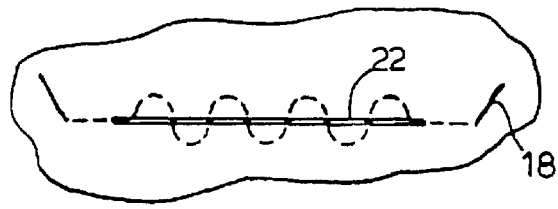
Figure 1E:
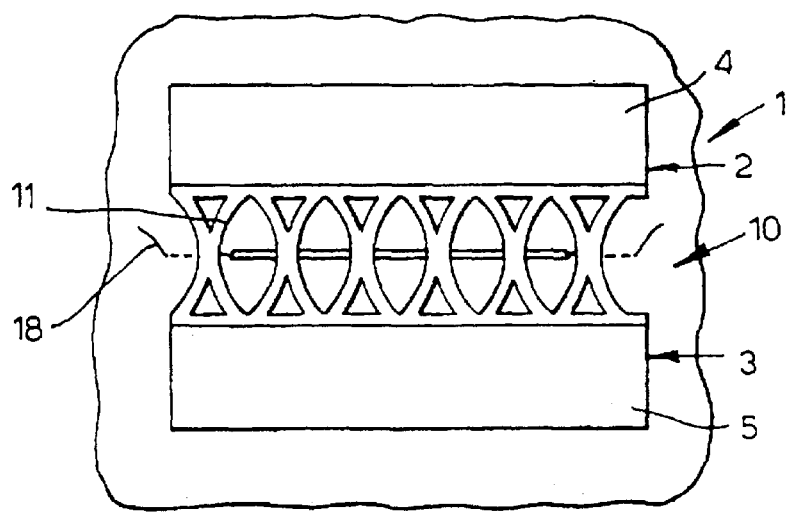
Figure 2:
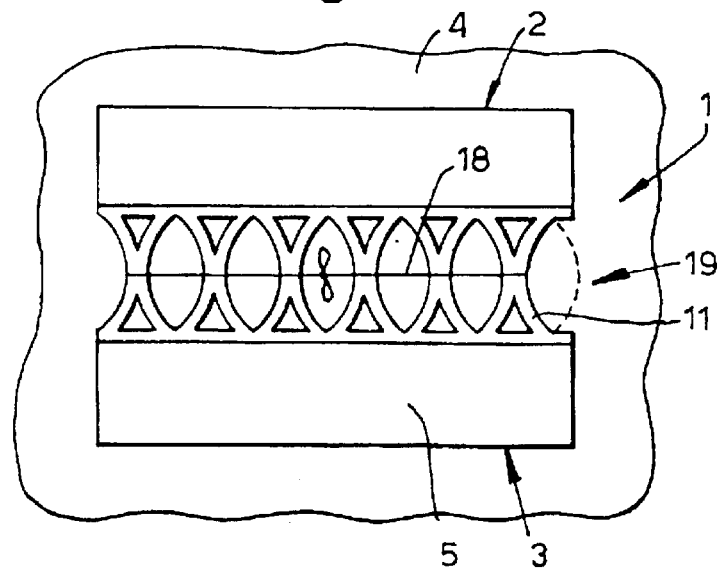
FIG. 2 shows the frame in FIG. 1e in more detail.

FIG. 1a shows a mole 21 surrounded by skin 20. FIG. 1b illustrates the incision limited by the wound/wound edges 22 made during removal of the mole/lesion. FIGS. 1c and 1d show the mole removed and illustrates the suturing with the intracutan technique (the stitches (the dotted line) remain beneath the skin). The suture threads 18 are not, however, attached to the skin, as per normal practice, but are left available at each end of the incision. In FIG. 1e the frame 1 is shown placed across the incision 22. The frame 1 is arranged on the skin with an adhesive 4,5, which can be for example an ordinary plaster material. The frame 1 is thus kept in place and creates an area with low tension around the closed wound. This means that the wound edges can be kept together more easily by the intradermal method. The suture threads 18 are gathered up from the surface of the skin at each end edge of the frame 1 and the thread is placed across the frame and knotted in the frame's middle part. By tying the thread 18 across the frame, the pull in the thread can be easily controlled, something which is very difficult when the thread is attached directly in the skin. Using the frame 1 allows the sutures to be kept in place (together with the adhesive) and the frame will keep the suture in place. Furthermore, the entire equipment is lifted off the wound, thus preventing it from growing into the wound.

Figure 3:
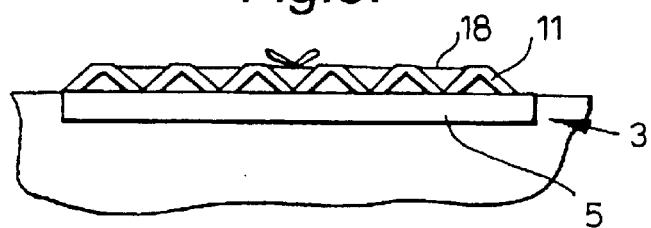
FIG. 3 shows the frame in FIG. 2 seen from the long side of the frame.
Figure 4:
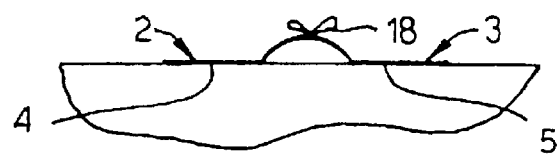
FIG. 4 shows the frame from the short end of the frame.
Figure 5:
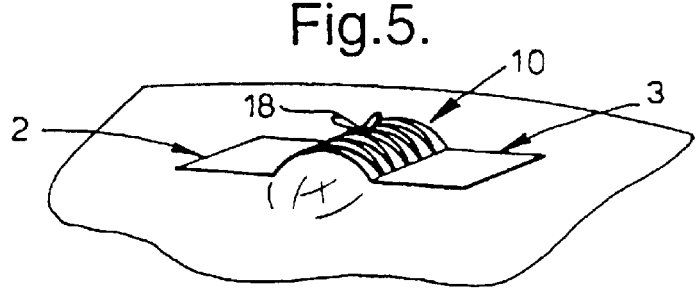
FIG. 5 shows the frame in perspective.

Reference is now made to FIGS. 2, 3, 4 and 5 where the frame in FIG. 1 is shown in more detail from different angles. The frame 1 comprises fixed foundation parts 2, 3 arranged with adhesive 4 and 5, respectively. Further a joining device 10 consisting of a braid 11, which can be formed of cloth, plastic material etc, is shown. Longitudinal suture thread 18 is also shown drawn across the joining device 10 and joined in the middle part thereof. Further, FIG. 3 shows a cross-section of the frame 1 and the arched/upward braiding 11 is clearly evident here with the longitudinal suture thread 18 lying on top of this.

FIGS. 6a and 6b show a second embodiment of the frame 1 seen from above and from the end respectively. The joining device 10 here can be arched or be flat braided 12. The foundation parts 2 and 3 here are both arranged with an adhesive 4 and 5 as in the first embodiment.

FIG. 7a shows a third embodiment of the frame 1 where the joining device 10 consists of crossribs 13. The crossribs 13 can be flat or smooth as shown in FIG. 7b or they can be arched or upward sloping in shape as shown in FIG. 7c. The crossribs can also be arranged with tracks 15 for the thread.

A fourth embodiment of the frame 1 is shown in FIG. 8 and consists of a joining device 10 which is built up of an arched braid 14 and connected with the first and second foundation parts 2, 3. Holes 8 are arranged in the foundation parts 2,3 to allow the crossing suture thread 19 to be threaded through these by use of the frame 1 in connection with cross sutures, which means the frame can be used both when the intracutan technique and ordinary suture technique are used. Longitudinal ribs 6, 7 are also shown arranged in connection with the first and second foundation parts 2, 3 respectively and the joining device 10.

FIG. 9 shows a fourth embodiment of the frame 1. The joining device 10 is comprised here of a material 16 which for example can be silicon or a medicine which is absorbed into the skin locally, for example steroids, thus reducing scar formation.

Common for all these embodiments of the frame 1 in accordance with the invention is that the first and second foundation parts 2, 3 are arranged with adhesives 4, 5 and a joining device 10, either arched or flat, and arranged between the two foundation parts 2, 3. The frame's construction causes it mainly to have a constant length, i.e. the frame cannot be pressed together or extended lengthways to any great degree. The frame will however be flexible, also lengthways, so that it follows the body's contours. Further, the frame's joining device has an elastic construction so that an almost constant pull in the thread is achieved, which is attached to the outside of the joining device, during varying stretch tension in the skin. Further, the frame can be cut into appropriate lengths, i.e. slightly longer than the wound, thus giving the correct direction to the pull on the thread.

The frame according to the invention combines the use of plaster and suture material. It works as an anchor for the sutures and thus simplifies the suture technique, particularly during intradermal technique. Further, the tension across the whole scar throughout the healing process is removed. The scar is framed and is protected against being pulled in all directions by the tape. The suture stabilizes the frame and the frame stabilizes the suture. Stitches can be removed early without removing the frame, which can then adapt the wound edge alone without the use of foreign material in the skin. The wound can be inspected at any time, as the frame does not cover the wound itself. The frame lifts all the equipment off the skin and thus prevents anything growing into the wound. Thus, the frame allows for optimal healing of a wound after minor surgical operations in areas of the skin with a lot of tension.

What is claimed is:

1. A frame for use in suturing of a wound, where the frame is placed on each side of the wound and reaches across the wound, the frame comprising:

first and second foundation parts for being placed on the skin along each side of the wound, respectively, wherein the first and second foundation parts are provided with an adhesive for securing the first and second foundation parts to the skin; and a joining device extending between the first and second foundation parts, the joining device comprising an upwardly protruding arched braid defining a cross pattern, and the joining device further comprising a flexible construction having a substantially constant length.

2. The frame as claimed in claim 1, wherein the first and second foundation parts comprise internal longitudinal ribs, respectively, which face the wound and are provided with an adhesive.

3. A frame for use in suturing of a wound, where the frame is placed on each side of the wound and reaches across the wound, the frame comprising:

first and second foundation parts for being placed on the skin on each side of and along the wound/wound edges, respectively, wherein the first and second foundation parts are provided with an adhesive for securing the first and second foundation parts to the skin; and a joining device extending between the first and second foundation parts, the joining device comprising a flat braiding defining a crisscross pattern, and the joining device further comprising a flexible construction having a substantially constant length.

4. The frame as claimed in claim 3, wherein the cross ribs are provided with grooves.

5. The frame as claimed in claim 4, wherein the first and second foundation parts comprise internal longitudinal ribs, respectively, which face the wound and are provided with an adhesive.

6. The frame as claimed in claim 3, wherein the first and second foundation parts comprise internal longitudinal ribs, respectively, which face the wound and are provided with an adhesive.

7. A frame for use in suturing of a wound, where the frame is placed on each side of the wound and reaches across the wound, the frame comprising:

first and second foundation parts for being placed on the skin on each side of and along the wound/wound edges, respectively, wherein the first and second foundation parts are provided with an adhesive for securing the first and second foundation parts to the skin; and a joining device extending between the first and second foundation parts, the joining device comprising a plurality of upward-arching cross ribs, and the joining device further comprising a flexible construction having a substantially constant length.

8. The frame as claimed in claim 7, wherein the first and second foundation parts comprise internal longitudinal ribs, respectively, which face the wound and are provided with an adhesive.

9. The frame as claimed in claim 7, wherein each of the first and second foundation parts are provided with a plurality of holes for receiving cross sutures.

10. A frame for use in suturing of a wound, where the frame is placed on each side of the wound and reaches across the wound, the frame comprising:

first and second foundation parts for being placed on the skin on each side of and along the wound/wound edges, respectively, wherein the first and second foundation parts are provided with an adhesive for securing the first and second foundation parts to the skin; and a joining device extending between the first and second foundation parts, the joining device comprising a plurality of flat cross ribs, and the joining device further comprising a flexible construction having a substantially constant length.

11. The frame as claimed in claim 10, wherein the first and second foundation parts comprise internal longitudinal ribs, respectively, which face the wound and are provided with an adhesive.

12. A frame for use in suturing of a wound, where the frame is placed on each side of the wound and reaches across the wound, the frame comprising:

first and second foundation parts for being placed on the skin on each side of and along the wound/wound edges, respectively, wherein the first and second foundation parts are provided with an adhesive for securing the first and second foundation parts to the skin; and a joining device extending between the first and second foundation parts, the joining device comprising a flexible construction having a substantially constant length, wherein the joining device comprises a material capable of entering the skin locally, and the material is silicone.

13. A frame for use in suturing of a wound, where the frame is placed on each side of the wound and reaches across the wound, the frame comprising:

first and second foundation parts for being placed on the skin on each side of and along the wound/wound edges, respectively, wherein the first and second foundation parts are provided with an adhesive for securing the first and second foundation parts to the skin; and a joining device extending between the first and second foundation parts, the joining device comprising a flexible construction having a substantially constant length, wherein the joining device comprises a medicine capable of entering the skin locally, and the medicine is a steroid.

14. A method of suturing a wound, the method comprising:

suturing the wound with intracutan suture technique while the threads are not attached to the skin and remain loose;

placing and fixing a frame across the wound such that a first foundation part and a second foundation part of the frame are located along each side of the wound, respectively, and an area of low tension around the closed wound is achieved, wherein the frame includes a joining device extending between the first and second foundation parts, and the first and second foundation parts are fixed to the skin by an adhesive;

pulling the threads up and tying the threads across the joining device, which has a substantially constant length; and removing the threads after a period of time, wherein the frame remains across the wound in order to reduce tensional stresses in the wound until it is sufficiently healed.

* * * * *